(12) United States Patent
Weiner et al.

(10) Patent No.: US 8,957,262 B2
(45) Date of Patent: Feb. 17, 2015

(54) OLEFIN HYDRATION FOR HYDROGENATION PROCESSES

(71) Applicant: Celanese International Corporation, Irving, TX (US)

(72) Inventors: Heiko Weiner, Pasadena, TX (US); James H. Zink, League City, TX (US); Mark O. Scates, Houston, TX (US)

(73) Assignee: Celanese International Corporation, Irving, TX (US)

( * ) Notice: Subject to any disclaimer, the term of this patent is extended or adjusted under 35 U.S.C. 154(b) by 259 days.

(21) Appl. No.: 13/681,866

(22) Filed: Nov. 20, 2012

(65) Prior Publication Data

US 2014/0142350 A1    May 22, 2014

(51) Int. Cl.
*C07C 29/149* (2006.01)
*C07C 29/04* (2006.01)

(52) U.S. Cl.
CPC .............. *C07C 29/149* (2013.01); *C07C 29/04* (2013.01)
USPC ....................................................... 568/885

(58) Field of Classification Search
CPC ................................................... C07C 29/149
USPC ........................................................ 568/885
See application file for complete search history.

(56) References Cited

U.S. PATENT DOCUMENTS

| | | |
|---|---|---|
| 1,469,447 A | 10/1923 | Schneible |
| 2,591,671 A | 4/1952 | Catterall |
| 2,591,672 A | 4/1952 | Catterall |
| 2,607,719 A | 8/1952 | Eliot et al. |
| 2,702,783 A | 2/1955 | Harrison et al. |
| 2,715,604 A | 8/1955 | Weaver, Jr. |
| 2,744,939 A | 5/1956 | Kennel |
| 2,801,209 A | 7/1957 | Muller et al. |
| 3,404,186 A | 10/1968 | Bailey et al. |
| 3,408,267 A | 10/1968 | Miller et al. |
| 3,445,345 A | 5/1969 | Katzen et al. |
| 3,686,334 A | 8/1972 | Britton |
| 3,953,533 A | 4/1976 | Sommer et al. |
| 3,990,952 A | 11/1976 | Katzen et al. |
| 4,003,952 A | 1/1977 | Foster et al. |
| 4,306,942 A | 12/1981 | Brush et al. |
| 4,329,520 A | 5/1982 | Kavasmaneck et al. |
| 4,351,970 A | 9/1982 | Sommer et al. |
| 4,395,576 A | 7/1983 | Kwantes et al. |
| 4,422,903 A | 12/1983 | Messick et al. |
| 4,448,644 A | 5/1984 | Foster et al. |
| 4,454,358 A | 6/1984 | Kummer et al. |
| 4,517,391 A | 5/1985 | Schuster et al. |
| 4,541,897 A | 9/1985 | Sommer et al. |
| 4,600,571 A | 7/1986 | McCarroll et al. |
| 4,678,543 A | 7/1987 | Houben et al. |
| 4,761,505 A | 8/1988 | Diana et al. |
| 4,774,365 A | 9/1988 | Chen et al. |
| 4,842,693 A | 6/1989 | Wheldon |
| 4,880,937 A | 11/1989 | Matsushita et al. |
| 4,943,354 A | 7/1990 | Osterburg et al. |
| 4,956,506 A | 9/1990 | Latimer |
| 5,035,776 A | 7/1991 | Knapp |
| 5,124,004 A | 6/1992 | Grethlein et al. |
| 5,185,481 A | 2/1993 | Muto et al. |
| 5,215,902 A | 6/1993 | Tedder |
| 5,250,271 A | 10/1993 | Horizoe et al. |
| 5,284,983 A | 2/1994 | Muto et al. |
| 5,349,096 A | 9/1994 | Cockman et al. |
| 5,449,440 A | 9/1995 | Rescalli et al. |
| 5,488,185 A | 1/1996 | Ramachandran et al. |
| 5,565,068 A | 10/1996 | Parker et al. |
| RE35,377 E | 11/1996 | Steinberg et al. |
| 5,684,216 A | 11/1997 | Haining |
| 6,072,090 A | 6/2000 | Cockman et al. |
| 6,462,231 B1 | 10/2002 | Yanagawa et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,632,330 B1 | 10/2003 | Colley et al. |
| 6,673,978 B2 | 1/2004 | Coute' et al. |
| 6,809,217 B1 | 10/2004 | Colley et al. |
| 6,812,372 B2 | 11/2004 | Janssen et al. |
| 7,160,831 B2 | 1/2007 | Vaughn et al. |
| 7,341,706 B2 | 3/2008 | Fuglerud et al. |
| 7,361,794 B2 | 4/2008 | Grosso |
| 7,553,397 B1 | 6/2009 | Colley et al. |
| 7,572,353 B1 | 8/2009 | Vander et al. |
| 7,594,981 B2 | 9/2009 | Ikeda |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,842,844 B2 | 11/2010 | Atkins |
| 7,947,746 B2 | 5/2011 | Scates et al. |
| 7,964,379 B2 | 6/2011 | Verser et al. |
| 8,002,953 B2 | 8/2011 | Lee et al. |
| 8,053,610 B2 | 11/2011 | Kikuchi et al. |
| 8,062,482 B2 | 11/2011 | Warner |
| 8,071,389 B2 | 12/2011 | Weck et al. |
| 8,088,832 B2 | 1/2012 | Melnichuk et al. |
| 8,129,436 B2 | 3/2012 | Tirtowidjojo et al. |
| 8,198,057 B2 | 6/2012 | Padgett |
| 8,232,440 B2 | 7/2012 | Holtzapple et al. |
| 8,288,596 B2 | 10/2012 | Garton et al. |
| 8,299,132 B2 | 10/2012 | Gracey et al. |
| 8,299,133 B2 | 10/2012 | Gracey et al. |
| 2007/0144886 A1 | 6/2007 | Sylvester et al. |
| 2008/0135396 A1 | 6/2008 | Blum |
| 2008/0207959 A1 | 8/2008 | Plante et al. |
| 2009/0166172 A1 | 7/2009 | Casey et al. |
| 2009/0259086 A1 | 10/2009 | Bailey et al. |
| 2011/0004034 A1 | 1/2011 | Daniel et al. |
| 2011/0046421 A1 | 2/2011 | Daniel et al. |
| 2011/0224462 A1 | 9/2011 | Ditzel et al. |

FOREIGN PATENT DOCUMENTS

| | | |
|---|---|---|
| CN | 1230458 | 10/1999 |
| CN | 201768393 | 3/2011 |
| CN | 102091429 | 6/2011 |
| CN | 101525272 | 5/2012 |
| DE | 2723611 | 11/1978 |
| EP | 0137749 | 4/1985 |
| EP | 0104197 | 5/1986 |
| EP | 2060553 | 5/2009 |
| JP | 2009-263356 | 11/2009 |
| JP | 2010-159212 | 7/2010 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |

*Primary Examiner* — Elvis O Price

(57) ABSTRACT

Processes for contacting an olefin feed stream, preferably comprising ethylene, with at least one stream from an ethanol production process that comprises water. The hydration reaction produces ethanol to improve overall ethanol yields from the hydrogenation acetic acid and esters thereof.

20 Claims, 6 Drawing Sheets

OLEFIN HYDRATION FOR HYDROGENATION PROCESSES

FIELD OF THE INVENTION

The present invention relates generally to hydrogenation for producing ethanol. In particular, the present invention relates to hydrating olefins by contacting an olefin stream with at least one stream that comprises water from an ethanol production process.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Hydration of ethylene is described in U.S. Pat. Nos. 3,686,334; 3,953,533; 4,003,952; 4,329,520; 4,351,970; 4,956,506; 5,349,096; 5,684,216; and 6,072,090. Instability in organic feed stock prices contributes to fluctuations in the cost of conventionally produced ethanol, making the need for alternative sources of ethanol production all the greater when feed stock prices rise. Starchy materials, as well as cellulose materials, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol stream, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol product and a stream of acetic acid and ethyl acetate, which is recycled to the hydrogenation reactor.

In addition impurities, water is co-produced with ethanol during hydrogenation and distillation of ethanol and water is difficult to obtain anhydrous ethanol that is more suitable for fuel applications. Membranes have been proposed to remove water, such as those described in U.S. Pub. No. 2008/0207959 and U.S. Pat. Nos. 7,732,173; 7,594,981; and 4,774,365.

The need remains for improved processes for efficiently producing ethanol and reducing water content.

SUMMARY OF THE INVENTION

In a first embodiment, the present invention is directed to a process for producing ethanol by hydrogenating an acetic acid feed stream in the presence of a first catalyst in a first reaction zone to form a crude alcohol product, separating at least a portion of the crude alcohol product in one or more columns to produce an alcohol product stream and a dilute alcohol stream comprising water, and contacting an olefin feed stream with at least a portion of the dilute alcohol stream in the presence of a second catalyst in a second reaction zone to form an alcohol corresponding to the olefin. The process may further comprise introducing the alcohol corresponding to the olefin into the one or more columns. The dilute acid stream may comprise more water, based on relative weight percent, than the alcohol product stream. The olefin feed stream may comprise one or more olefins selected from the group consisting of ethylene, propylene, but-1-ene, pent-1-ene, and hex-1-ene. The hydrogenation and contacting step may produce the same alcohol. At least 5% of the olefin stream may be converted to the alcohol corresponding to the olefin. The molar ratio of water to olefin in the second reaction zone may be from 0.5:1 to 20:1. The second reaction zone may be conducted in the vapor phase. The second catalyst may be selected from the group consisting of phosphoric acid, sulfuric acid, tungstic acid, heteropoly acid salt and anionic ion exchange resin. The temperature of the second reaction zone may be from 150° C. to 600° C. The pressure of the second reaction zone may be from 1 MPa to 25 MPa. The process may further comprise dehydrating a portion of the alcohol product to produce the olefin feed stream. The first catalyst may comprise a first metal selected from the group consisting of cobalt, nickel, rhodium, palladium, osmium, iridium, platinum, titanium, zinc, chromium, rhenium, molybdenum, and tungsten; a second metal selected from the group consisting of molybdenum, tin, chromium, cobalt, vanadium, tungsten, palladium, platinum, lanthanum, cerium, manganese, rhenium, gold, and nickel, provided that the second metal is different than the first metal; and a support. The first catalyst may further comprise at least one support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In some embodiments, the support modifier may be calcium metasilicate. In other embodiments, the support modifier may be selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $Nb_2O_5$, $MnO_2$, $CuO$, $Co_2O_3$, and $Bi_2O_3$.

In other embodiments, the process may comprise providing a crude alcohol product comprising water that is further separated in one or more columns to produce an alcohol product stream and a dilute alcohol stream comprising water. The olefin feed stream is contacted with at least a portion of the dilute alcohol stream in the presence of a second catalyst in a second reaction zone to form an alcohol corresponding to the olefin.

In a second embodiment, the present invention is directed to a process for producing ethanol by hydrogenating an acetic acid feed stream in the presence of a first catalyst in a first reaction zone to form a first crude product comprising ethanol and water, contacting an olefin feed stream with at least a portion of the first crude product in the presence of a second catalyst in a second reaction zone to form a second crude product, wherein the second crude product comprises less water than the first crude product, and recovering ethanol from the second crude product. Conversion of acetic acid in the first reaction zone may be greater than 90% and the water concentration of the first crude product may be reduced by at least 5 wt. %.

In a third embodiment, the present invention is directed to a process for producing ethanol by hydrogenating an acetic acid feed stream in the presence of a first catalyst in a first reaction zone to form a crude ethanol stream, separating at least a portion of the crude ethanol stream in one or more columns to yield an ethanol product and a water stream, and contacting an olefin feed stream with at least a portion of the ethanol product in the presence of a second catalyst in a second reaction zone to form a dehydrated ethanol product, wherein the dehydrated ethanol product comprises less water than the ethanol product.

In a fourth embodiment, the present invention is directed to a process for producing ethanol by hydrogenating an acetic acid feed stream in the presence of a first catalyst in a first reaction zone to form a crude ethanol stream, separating at least a portion of the crude ethanol stream in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, separating at least a portion of the second residue in a third column into a third distillate comprising ethanol and a third residue comprising water, and contacting an olefin feed stream with at least a portion of the second residue, the third residue, or mixtures thereof in the presence of a second catalyst in a second reaction zone to form an alcohol corresponding to the olefin.

In a fifth embodiment, the present invention is directed to a process for producing ethanol by hydrogenating an acetic acid feed stream in the presence of a first catalyst in a first reaction zone to form a crude ethanol stream, separating at least a portion of the crude ethanol stream in a first column into a first distillate comprising ethanol, water and ethyl acetate, and a first residue comprising acetic acid, separating at least a portion of the first distillate in a second column into a second distillate comprising ethyl acetate and a second residue comprising ethanol and water, separating at least a portion of the second residue in a third column into a third distillate comprising ethanol and a third residue comprising water, and contacting an olefin feed stream with at least a portion of the third distillate in the presence of a second catalyst in a second reaction zone to form a dehydrated ethanol product, wherein the dehydrated ethanol product comprises less water than the third distillate.

In a sixth embodiment, the present invention is directed to a process for producing ethanol by hydrogenating acetic acid in the presence of a first catalyst in a first reaction zone to form a crude ethanol stream, separating at least a portion of the crude ethanol stream in a first column to yield a first residue comprising acetic acid and a substantial portion of the water from the crude ethanol stream and a first distillate comprising ethanol, ethyl acetate, and water, removing water from at least a portion of the first distillate to yield an ethanol mixture stream and a water stream, separating the ethanol mixture stream in a second column to yield a second residue comprising ethanol and a second distillate comprising ethyl acetate, and contacting an olefin feed stream with at least a portion of the first residue, the water stream, or mixtures thereof in the presence of a second catalyst in a second reaction zone to form an alcohol corresponding to the olefin.

In a seventh embodiment, the present invention is directed to a process for producing ethanol by hydrogenating acetic acid in the presence of a first catalyst in a first reaction zone to form a crude ethanol stream, separating at least a portion of the crude ethanol stream in a first column to yield a first residue comprising acetic acid and a first distillate comprising ethanol, ethyl acetate, and water, removing water from at least a portion of the first distillate to yield an ethanol mixture stream and a water stream, separating the ethanol mixture stream in a second column to yield a second residue comprising water and a second distillate comprising ethanol, and contacting an olefin feed stream with at least a portion of the second residue in the presence of a second catalyst in a second reaction zone to form a dehydrated ethanol product, wherein the dehydrated ethanol product comprises less water than the second residue.

In an eighth embodiment, the present invention is directed to a process for producing ethanol by hydrogenating acetic acid in the presence of a first catalyst in a first reaction zone to form a crude ethanol stream, separating at least a portion of the crude ethanol stream in a first column to yield a first distillate comprising ethyl acetate and a first residue comprising ethanol, acetic acid and water, separating at least a portion of the first residue in a second column into a second distillate comprising ethanol and a second residue comprising acetic acid and water, and contacting an olefin feed stream with a hydrating stream comprising at least a portion of the second residue in the presence of a second catalyst in a second reaction zone to form an alcohol corresponding to the olefin.

In a ninth embodiment, the present invention is directed to a process for producing ethanol by hydrogenating acetic acid in the presence of a first catalyst in a first reaction zone to form a crude ethanol stream, separating at least a portion of the crude ethanol stream in a first column to yield a first distillate comprising ethyl acetate and a first residue comprising ethanol, acetic acid and water, separating at least a portion of the first residue in a second column into a second distillate comprising ethanol and a second residue comprising acetic acid and water, and reacting an olefin feed stream with at least a portion of the second distillate in the presence of a second catalyst in a second reaction zone to form a dehydrated ethanol product, wherein the dehydrated ethanol product comprises less water than the second distillate

BRIEF DESCRIPTION OF DRAWINGS

The invention is described in detail below with reference to the appended drawings.

DETAILED DESCRIPTION OF THE INVENTION

Introduction

The present invention relates to processes for producing ethanol via the hydrogenation of acetic acid in the presence of a catalyst. Water is co-produced in equal molar ratios with the ethanol and thus water is present in the crude ethanol stream, ethanol product stream and intermediate streams, such as a dilute alcohol stream. An olefin feed stream is contacted with at least one of those streams in a reaction zone. The olefin feed stream produces alcohol and reduces the water concentration in those streams. This may lead to improved ethanol production and/or reduced separation requirements to recover ethanol.

During recovery of ethanol from the crude ethanol stream, there may be one or more intermediate streams that contain water. In general, these intermediate streams would normally be purged from the separation. Hydrating the olefin using the water in the intermediate stream may further improve alcohol production and/or ethanol recovery. In addition, the crude ethanol stream may also be contacted with an olefin and the ethanol product stream may be contacted with an olefin.

Although other production processes may use hydration of olefins to produce ethanol, those processes use relatively pure water streams for contacting with the olefin. The present invention integrates hydration with hydrogenation to improve ethanol yields and reduce the amount of water in the ethanol production process. Several of the streams resulting from the hydrogenation of acetic acid may contain water and thus may be suitable for contacting with an olefin.

In one embodiment, the intermediate stream is a dilute alcohol stream that comprises more water, based on relative weight percent, than the alcohol product stream. For example, the dilute alcohol stream may comprise at least 60 wt. % water, e.g., at least 80 wt. % or at least 90%. The dilute alcohol stream may also contain a minor amount of ethanol; that is less than 5 wt. % ethanol, e.g., less than 3 wt. % or less than 1 wt. %. In some embodiments, the dilute alcohol stream may be used as an extractive agent.

The stream that is contacted with the olefin preferably contains a low concentration of acetic acid, such as less than 20 wt. % acetic acid, e.g., less than 5 wt. % acetic acid or less than 1 wt. % acetic acid. Although not limited, it is preferred that the crude ethanol stream is contacted with an olefin under high acetic acid conversion conditions, such as greater than 90% or greater than 95%.

Figure 1A:
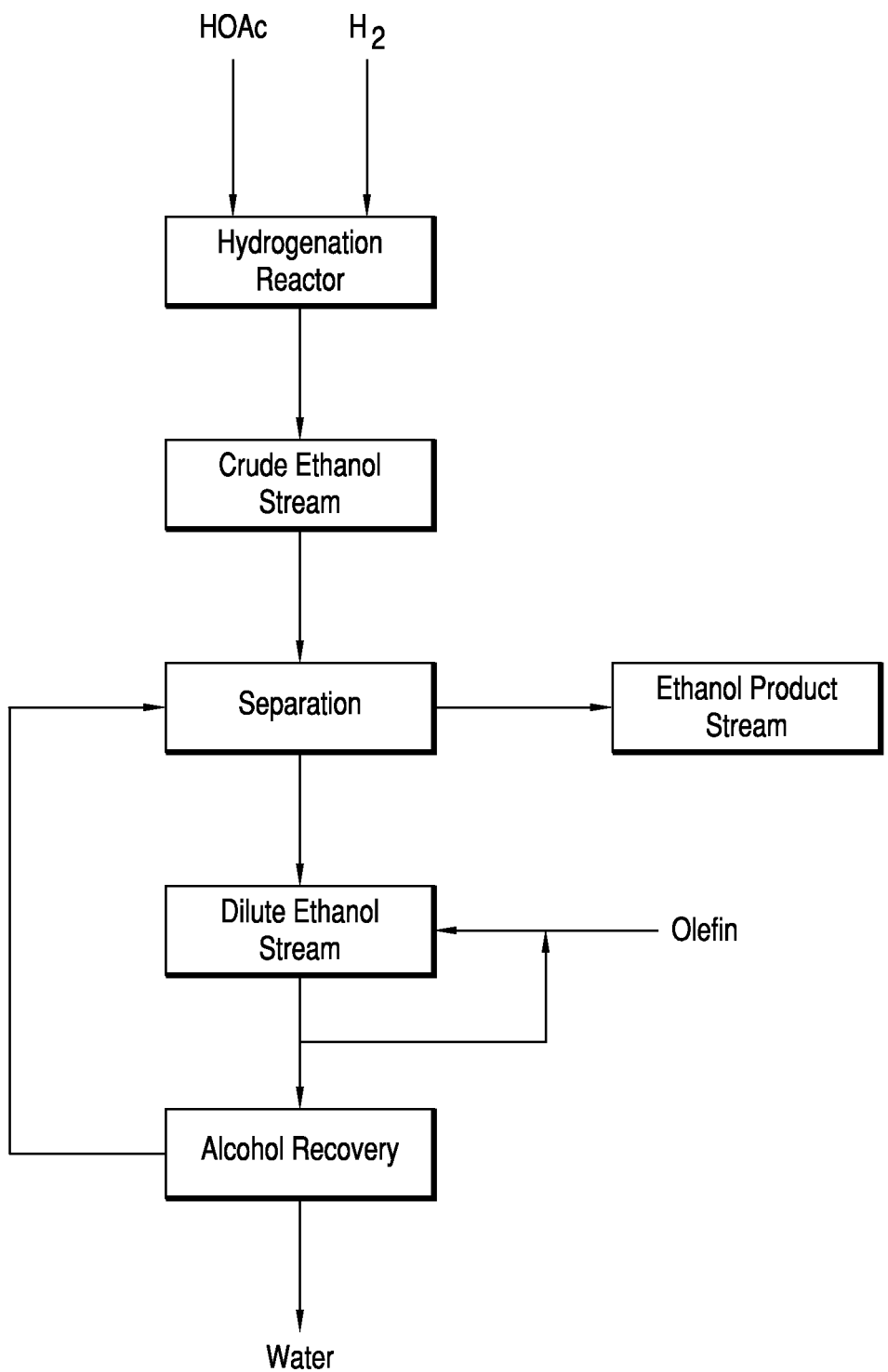
FIGS. 1A-1C are general flow diagrams in accordance with an embodiment of the present invention.
Figure 1B:
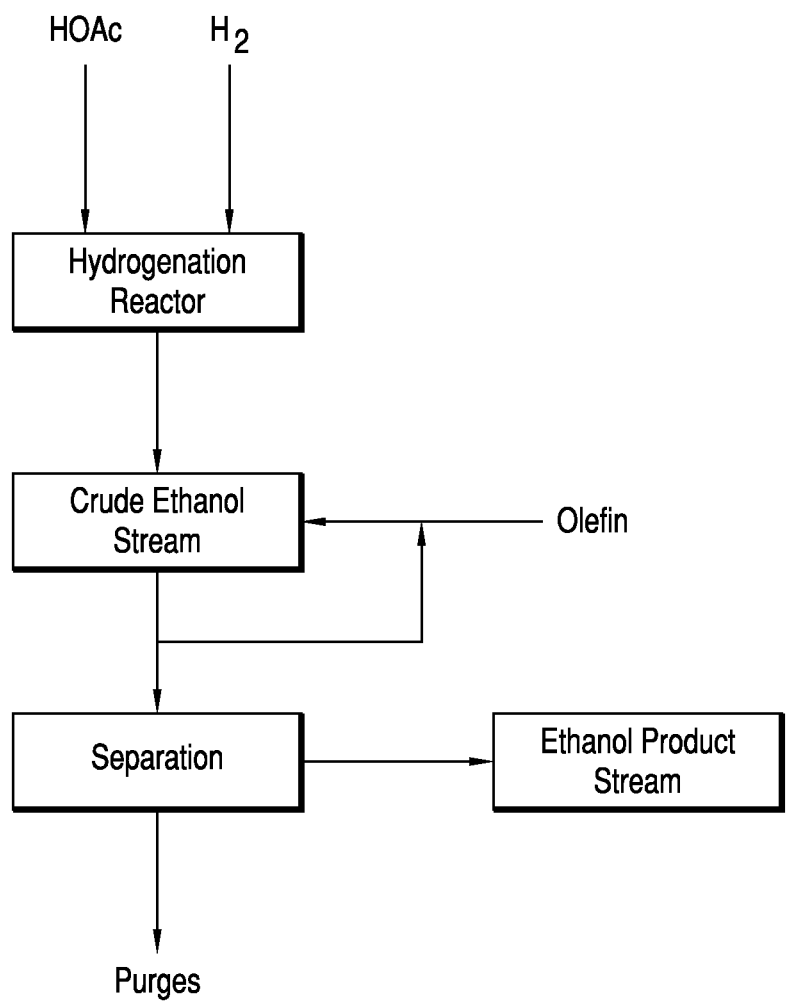
Figure 1C:
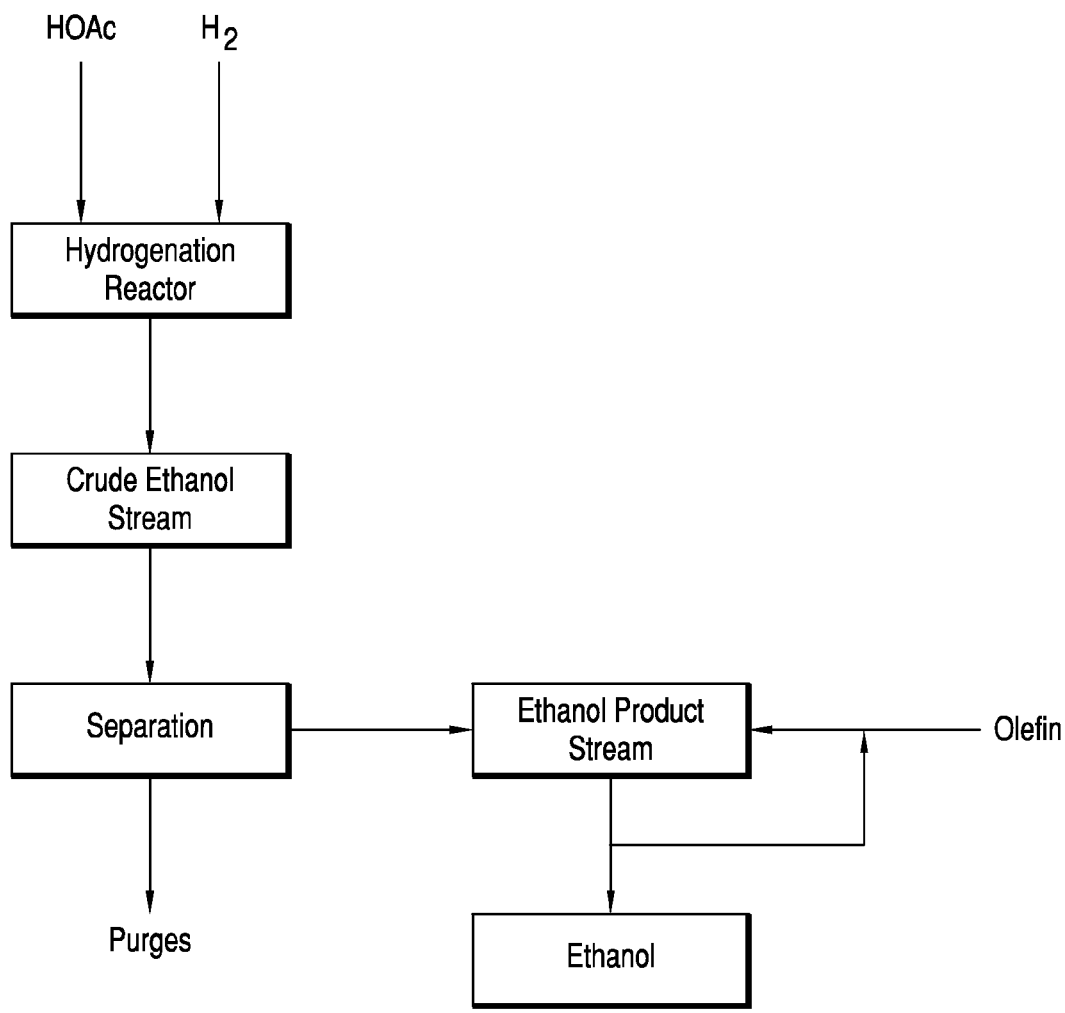

FIGS. 1A-1C are general flow diagrams of embodiments that contact an olefin with one of the streams. It should be appreciated that various combinations of these embodiments, may be utilized within the scope of this invention. For example, both the dilute alcohol stream and ethanol product stream may be contacted with an olefin. In FIG. 1A, acetic acid and hydrogen are reacted to produce a crude ethanol stream that is separated to recover an ethanol product stream and a dilute alcohol stream. The dilute alcohol stream is contacted with an olefin feed stream in a secondary hydration reaction zone to produce a hydration product. The olefin may be recovered from the hydration product and recycled as needed. The corresponding alcohol to the olefin, preferably ethanol, may be recovered and returned to the hydrogenation separation and the ethanol is ultimately recovered in the ethanol product stream. Water may be removed and purged as needed.

In FIG. 1B, the olefin feed stream may be reacted with the crude ethanol stream. Preferably hydrogen is removed from the crude ethanol stream prior to hydration with the olefin feed stream. The olefin may be recovered and recycled as needed. The remaining stream is forwarded to the hydrogenation separation to recover ethanol. Any other compound that is separated may be recycled to the hydrogenation reactor or purged as needed. The remaining stream may contain relatively less water than the crude ethanol stream, and preferably at least 5 wt. % less, e.g., at least 10 wt. % less. In addition, the remaining stream may also contain relatively more ethanol than the crude ethanol stream, and preferably at least 5 wt. % more, e.g., at least 10 wt. % more. The additional ethanol, and/or less water, may reduce the capital and energy requirements to recover the ethanol product stream.

In FIG. 1C, the olefin feed stream may be reacted with the ethanol product stream. In using distillation, the recovered ethanol may contain from 3 to 12 wt. % water. To reduce the water concentration, an olefin feed stream may be reacted with the ethanol product stream. The resulting ethanol product, also referred to as a dehydrated ethanol product, may be enriched in ethanol by at least 5%, e.g., at least 10%. Also, the olefin may be recovered and recycled as needed.

In one embodiment, the olefin feed stream is one or more olefins selected from the group consisting of ethylene, propylene, but-1-ene, pent-1-ene, and hex-1-ene. Each of the olefins produces the corresponding alcohol. Ethylene is preferred because it produces ethanol when hydrated. Advantageously, this may allow increase production from the water co-produced with ethanol during hydrogenation. In one embodiment, the olefin feed stream comprises at least 85 mol. % ethylene, e.g. at least 90 mol. % ethylene, or at least 95 mol. % ethylene. The olefin feed stream may comprise a mixture of ethylene and propylene, in a molar ratio of ethylene to propylene of greater than 8:1, e.g., greater than 10:1 or greater than 15:1. The olefin feed stream may also contain minor amounts of alkanes such as methane, ethane, propane, or mixtures thereof. For example, a suitable ethylene stream may comprise 98.5 mol. % ethylene, 0.4 mol. % methane, 1 mol. % ethane, and 0.1 mol. % propane.

In the hydration reaction zone, the molar ratio of water to olefin may be from 0.5:1 to 20:1, e.g., from 0.3:1 to 3:1. In some embodiments, an excess of ethylene may favor an increase production of ethanol. The olefin hydration is preferably conducted in the vapor phase. If necessary, the stream contacted with the olefin may be withdrawn from the hydrogenation separation as a vapor stream (such as steam) or may be vaporized prior to the hydrating reaction zone. In general, lower temperatures and higher pressures may favor high equilibrium yields for the hydration reaction. The olefin hydration reaction is exothermic and is carried out at a temperature from 150° C. to 600° C., e.g., from 200° C. to 300° C. Within this temperature range, the hydration of ethylene may carried out at a temperature from above its dew point (−45.6° C.) to 350° C., and preferably from 200° C. to 300° C. The hydration of propylene or but-1-ene may carried out at a temperature from above its dew point (−56.7° C.) to 300° C., e.g., from 150° C. to 250° C. or from 150° C. to 220° C. The hydration reaction is carried out at a pressure from 1 to 25 MPa, e.g., from 2 to 10 MPa. Within this range, the hydration of ethylene may carried out at a pressure from 3 to 10 MPa. In addition, the hydration of propylene or but-1-ene may be carried out at a slightly lower pressure from 2 to 8 MPa, e.g., from 2 to 5 MPa.

Catalysts for the hydration reaction may include phosphoric acid, sulfuric acid, tungstic acid, heteropoly acid salt and anion ion exchange resin catalyst. More specific examples of suitable catalysts may include solid silicon dioxide coated with phosphoric(V) acid, alumina and tungstic oxide, ion-exchanged montmorillonites, such as Al-montmorillonites, and zeolites. Phosphoric(V) acid catalysts are widely used and suitable for the present invention. The hydration catalyst may be a supported catalyst on a support material selected from celite, silica, alumina, zeolite, and combinations thereof. Suitable catalysts are also disclosed in U.S. Pat. Nos. 3,953,533; 4,329,520; 4,351,970; 5,349,096; 5,684,216; 6,072,090; and 7,148,179, the entire contents and disclosure of which is hereby incorporated by reference. In one embodiment the catalyst for the hydration reaction is different than the hydrogenation reaction. The catalysts should be sufficiently stabilize to convert at least 5% of the water from the dilute alcohol stream to the alcohol corresponding to the olefin, e.g. at least 10% or at least 25%. In some embodiments, the unreacted olefin may be recycled to further increase conversion.

Hydrogenation of Acetic Acid

The hydration processes of the present invention may be used with any hydrogenation process for producing ethanol. The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. In one embodiment, the production of ethanol may be integrated with a methanol carbonylation processes.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol stream may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Black liquor, which is an aqueous solution of lignin residues, hemicellulose, and inorganic chemicals, may also be used as a biomass source. Biomass-derived syngas has a detectable $^{14}C$ isotope content as compared to fossil fuels such as coal or natural gas.

In another embodiment, the acetic acid used in the hydrogenation step may be formed from the fermentation of biomass. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference.

The acetic acid fed to the hydrogenation reactor may also comprise acetic anhydride, acetaldehyde, ethyl acetate, propionic acid, water, and mixtures thereof.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

In preferred embodiments, the catalyst is employed in a fixed bed reactor where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C. The hydrogenation reactor pressure may range from 10 kPa to 3000 kPa, e.g., from 50 kPa to 2300 kPa. In one embodiment, the hydrogenation reaction is carried out at a pressure that is less than the hydration reaction pressure. The reactants may be fed to the reactor at a gas hourly space velocity (GHSV) ranging from 50 $hr^{-1}$ to 50,000 $hr^{-1}$, e.g., from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 20:1 to 1:2, or from 18:1 to 2:1.

The hydrogenation of acetic acid to form ethanol is preferably conducted in the presence of a hydrogenation catalyst in the reactor. As indicated herein, the hydrogenation catalyst, also referred to herein as "first catalyst," is different than the hydration catalyst used to react the olefin stream and water, also referred to herein as "second catalyst." In one embodiment, the hydrogenation catalyst may be a bifunctional catalyst and may convert acetic acid and ethyl acetate. The catalysts preferably are not methanol synthesis catalysts and are substantially free of copper and/or zinc, including oxides thereof. Suitable hydrogenation catalysts include catalysts comprising a first metal, a second metal, and optionally a third metal and on a catalyst support. Preferred bimetallic combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, nickel/palladium, gold/palladium, ruthenium/rhenium, and ruthenium/iron. Additional metal combinations may include palladium/rhenium/tin, palladium/rhenium/cobalt, palladium/rhenium/nickel, platinum/tin/palladium, platinum/tin/cobalt, platinum/tin/chromium, and platinum/tin/nickel. Exemplary hydrogenation catalysts are further described in U.S. Pat. Nos. 7,608,744 and 7,863,489 and U.S. Pub. No. 2010/0197985, the entireties of which are incorporated herein by reference.

In one embodiment, the hydrogenation catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. The first metal may be selected from the group consisting of platinum, palladium, cobalt, nickel, and ruthenium. The first metal may be present in the catalyst in an amount from 0.1 to 10 wt. %, e.g., from 0.1 to 5 wt. %, or from 0.1 to 3 wt. %.

The hydrogenation catalyst may further comprise a second metal selected from the group consisting of copper, molybdenum, tin, chromium, iron, cobalt, vanadium, tungsten, palladium, platinum, lanthanum, cerium, manganese, ruthenium, rhenium, gold, and nickel. Preferably, the second metal is different than the first metal. The second metal preferably is present in an amount from 0.1 to 20 wt. %, e.g., from 0.1 to 10 wt. %, or from 0.1 to 5 wt. %.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 7.5 wt. %, e.g., from 0.1 to 5 wt. %, or from 0.1 to 4 wt. %.

In addition to one or more metals, in some embodiments of the present invention the catalysts further comprise a support or a modified support. As used herein, the term "modified support" refers to a support that includes a support material and a support modifier, which adjusts the acidity of the support material. Modified supports are further described in US Pub. No. 2010/0121114, the entire contents and disclosures of which are hereby incorporated by reference.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst.

Suitable support materials may include, for example, include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$).

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a mole percentage based on acetic acid in the feed. The conversion may be at least 40%, e.g., at least 60%, or at least 80%. Higher conversions of greater than 90% may be required when the crude ethanol stream is contacted with the olefin feed stream. In those embodiments, it is preferred to achieve very high conversions that approach near 100% conversion.

Selectivity is expressed as a mole percent based on converted acetic acid. It should be understood that each compound converted from acetic acid has an independent selectivity and that selectivity is independent from conversion. In one embodiment, catalyst selectivity to ethanol is at least 60%, e.g., at least 70%, or at least 80%. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. A productivity from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol stream produced by the reactor, before any subsequent processing, such as purification and separation, will typically comprise the exemplary compositional ranges provided in Table 1. In one embodiment, the hydrogenation of acetic acid produces little, if any olefins as such as ethylene. The "others" identified in Table 1 may include, for example, esters, ethers, aldehydes, ketones, alkanes, and carbon dioxide.

TABLE 1

CRUDE ETHANOL STREAM COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol stream may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %.

Ethanol Separation

Ethanol produced from hydrogenation may be recovered using several different techniques. The separation zone of FIG. 2 uses four columns. The separation zone of FIG. 3 employs two columns with an intervening water separation.

Figure 3:
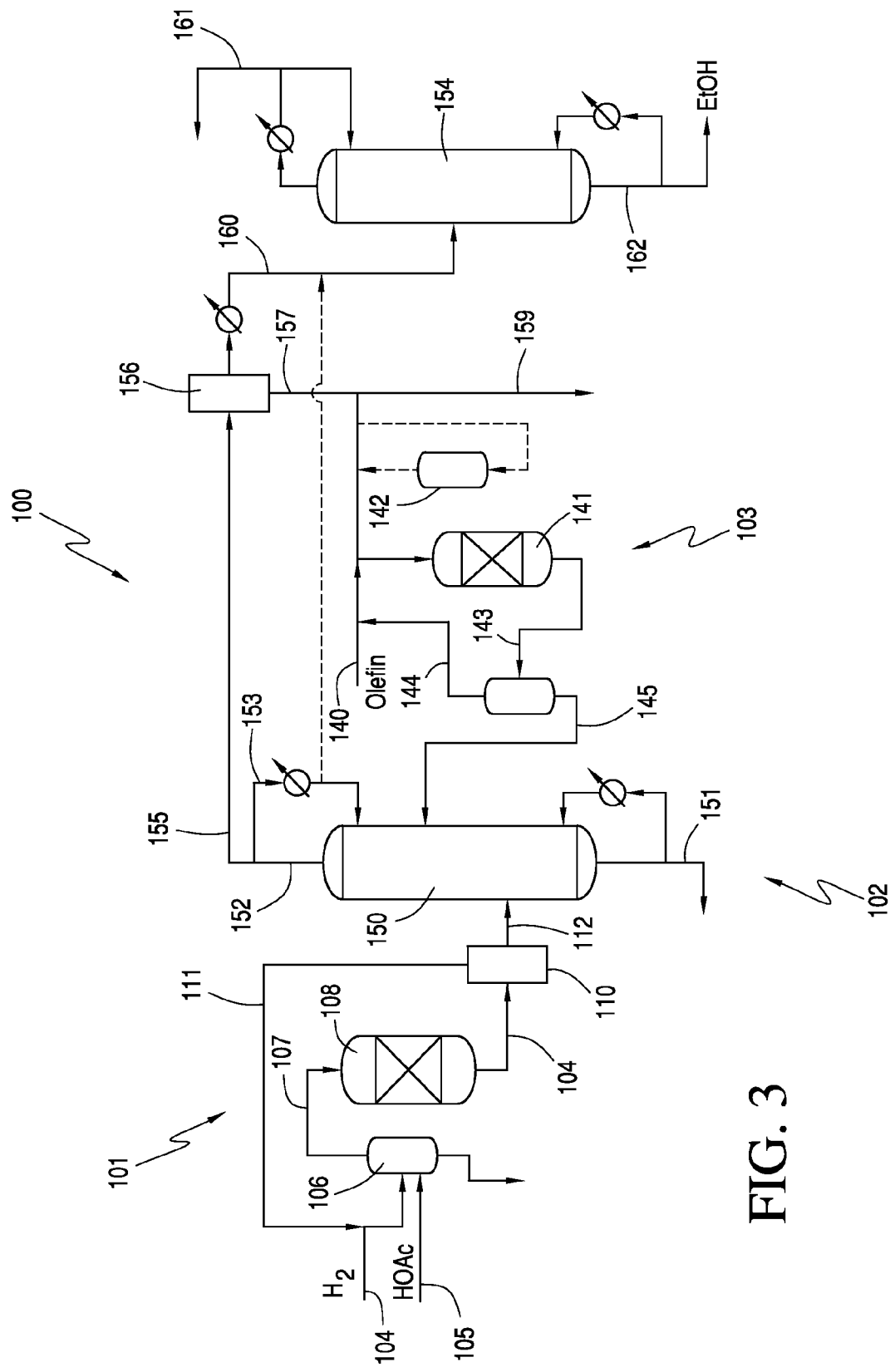
FIG. 3 is a schematic diagram of another ethanol production process in accordance with an embodiment of the present invention.
Figure 4:
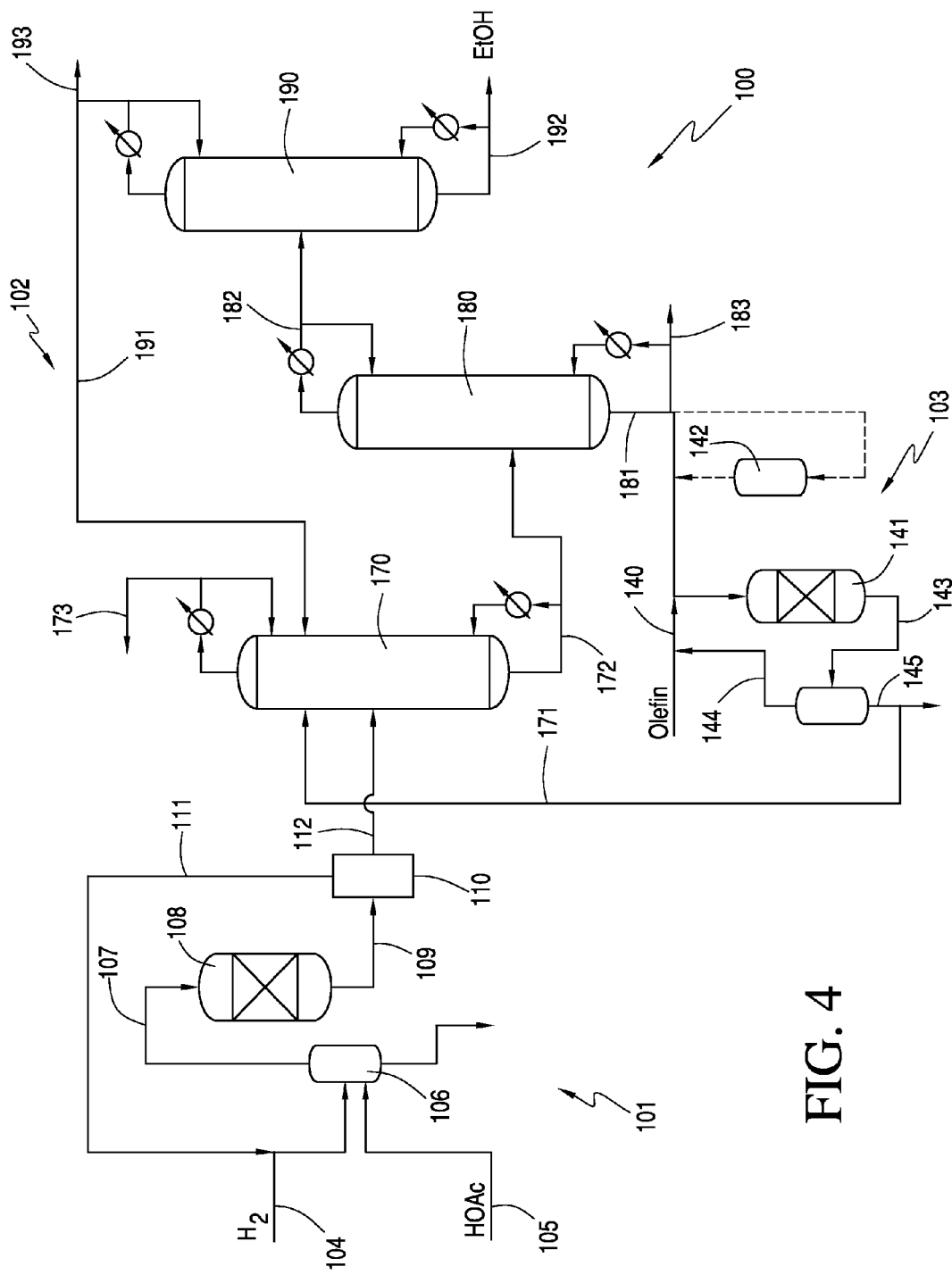
FIG. 4 is a schematic diagram of another ethanol production process in accordance with an embodiment of the present invention.

The separation zone of FIG. 4 uses three columns. In some embodiment, the intervening water separation may also be used in FIG. 4. Other separation systems may also be used with embodiments of the present invention. For purposes of illustration, contacting a dilute alcohol stream with an olefin feed stream as shown in FIG. 1A is demonstrated in FIGS. 2-4. In other embodiments, FIG. 1B or 1C may be combined with the specific separation schemes shown in FIGS. 2-4. Various recovery systems are described in US Pub. No. 2011/0190547, 2011/0190548, 2011/0275864, and 2012/0010438, the entire contents and disclosure of which is hereby incorporated by reference.

Figure 2:
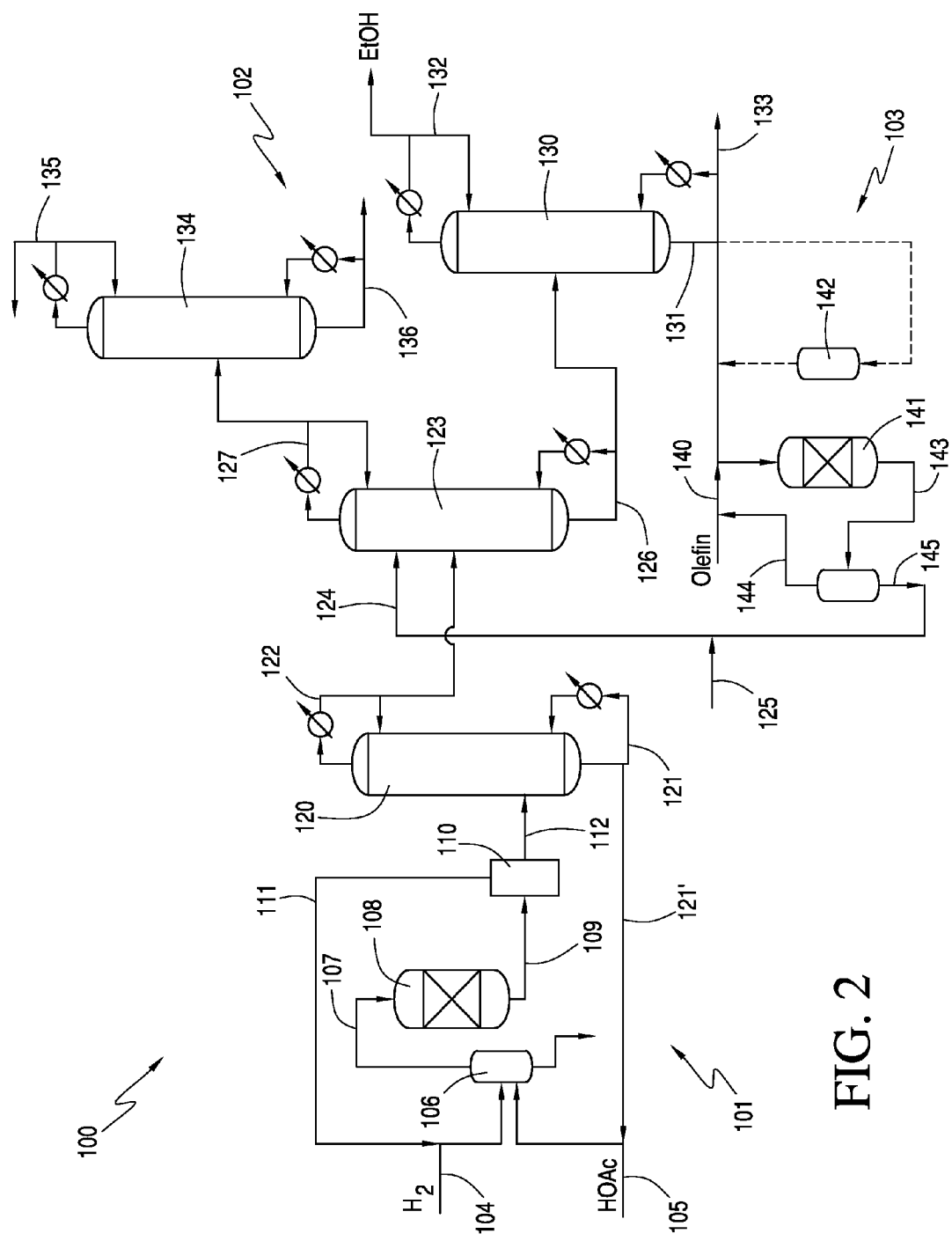
FIG. 2 is a schematic diagram of an ethanol production process in accordance with an embodiment of the present invention.

Referring to FIG. 2, hydrogenation system 100 includes a hydrogenation reaction zone 101, separation zone 102, and hydration reaction zone 103. Hydrogen and acetic acid via lines 104 and 105, respectively, are fed to a vaporizer 106 to create a vapor feed stream in line 107 that is directed to reactor 108. Hydrogen feed line 104 may be preheated to a temperature from 30° C. to 150° C. and a pressure from 1300 kPa to 3100 kPa. Acetic acid in line 105 may comprise fresh acetic acid, i.e., acetic acid that has not been previously exposed to a hydrogenation catalyst. Reactor 108 is a shell and tube reactor. Although one reactor is shown in FIGS. 2-4, multiple reactors and reactor beds may be used for in the hydrogenation reaction zone 101. In one embodiment, lines 104 and 105 may be combined and jointly fed to vaporizer 106. The temperature of the vapor feed stream in line 107 is preferably from 100° C. to 350° C.

As discussed above, reactor 108 contains the catalyst that is used in the hydrogenation of acetic acid. In one embodiment, the catalyst is preferably contained in a shell portion of reactor 108. During the hydrogenation process, a crude ethanol stream is withdrawn, preferably continuously, from reactor 108 via line 109.

Crude ethanol stream 109 may be condensed and fed to separator 110, which, in turn, provides a vapor stream 111 and a liquid stream 112. In some embodiments, separator 110 may be a flasher or a knockout pot. Separator 110 may operate at a temperature from 20° C. to 250° C., e.g., from 30° C. to 225° C., and a pressure from 50 kPa to 2000 kPa, e.g., from 75 kPa to 1500 kPa.

Vapor stream 111 exiting separator 110 may comprise hydrogen and hydrocarbons, and may be purged and/or returned to reaction zone 101 with hydrogen feed 104. In some embodiments, the returned vapor stream 111 may be compressed before being combined with hydrogen feed 104.

In FIG. 2, liquid stream 112 from separator 110 is withdrawn and pumped to the side of first column 120, also referred to as an "acid separation column." In one embodiment, the contents of liquid stream 112 are substantially similar to the crude ethanol stream obtained from the reactor, except that the composition has been depleted of hydrogen, carbon dioxide, methane and/or ethane, which are removed by separator 110. Accordingly, liquid stream 112 may also be referred to as a crude ethanol stream. Exemplary components of liquid stream 112 are provided in Table 2. It should be understood that liquid stream 112 may contain other components, not listed in Table 2.

TABLE 2

| COLUMN FEED COMPOSITION (Liquid Stream 112) | | | |
|---|---|---|---|
| | Conc. (wt. %) | Conc. (wt. %) | Conc. (wt. %) |
| Ethanol | 5 to 70 | 10 to 60 | 15 to 50 |
| Acetic Acid | <90 | 5 to 80 | 5 to 70 |
| Water | 5 to 30 | 5 to 28 | 10 to 26 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification may not be present and if present may be present in amounts greater than 0.0001 wt. %.

In one optional embodiment, crude ethanol stream 109 or liquid stream 112 from FIGS. 2-4 may be reacted in a hydration reaction zone with an olefin feed stream as described above in FIG. 1B.

In the embodiment shown in FIG. 2, line 112 is introduced to the lower part of first column 120. In first column 120, unreacted acetic acid, a portion of the water, and other heavy components, if present, are removed from the composition in line 112 and are withdrawn, preferably continuously, as residue in line 121. Some or all of the residue may be returned and/or recycled back to reaction zone 101 via line 121'. Recycling the acetic acid in line 121' to the vaporizer 106 may reduce the amount of heavies that need to be purged from vaporizer 106. Reducing the amount of heavies to be purged may improve efficiencies of the process while reducing byproducts.

First column 120 also forms an overhead distillate, which is withdrawn in line 122, and which may be condensed and refluxed, for example, at a ratio from 10:1 to 1:10.

When column 120 is operated under standard atmospheric pressure, the temperature of the residue exiting in line 121 preferably is from 95° C. to 120° C., e.g., from 110° C. to 117° C. The temperature of the distillate exiting in line 122 preferably is from 70° C. to 110° C., e.g., from 75° C. to 95° C. First column 120 preferably operates at ambient pressure. In other embodiments, the pressure of first column 120 may range from 0.1 kPa to 510 kPa. Exemplary components of the distillate and residue compositions for first column 120 are provided in Table 3 below. For convenience, the distillate and residue of the first column may also be referred to as the "first distillate" or "first residue." The distillates or residues of the other columns may also be referred to with similar numeric modifiers (second, third, etc.) to distinguish them from one another, but such modifiers should not be construed as requiring any particular separation order.

TABLE 3

| ACID COLUMN 120 (FIG. 2) | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |

TABLE 3-continued

ACID COLUMN 120 (FIG. 2)

|  | Conc. (wt. %) | Conc. (wt. %) | Conc. (wt. %) |
|---|---|---|---|
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

The distillate in line 122 preferably comprises ethanol, ethyl acetate, and water, along with other impurities, which may be difficult to separate due to the formation of binary and tertiary azeotropes. To further separate distillate, line 122 is introduced to the second column 123, also referred to as the "light ends column," preferably in the middle part of column 123. Preferably second column 123 is an extractive distillation column, and an extraction agent is added thereto, via line 124. The extractive agent comprises water. The extractive agent may be obtained from hydration reaction zone 103 or third residue 131. In some embodiments, the extraction agent is fed from a source outside of process 100 via optional line 125 to second column 123.

In a tray column, the extractive agent in line 124 is continuously added near the top of second column 123 so that an appreciable amount of the extractive agent is present in the liquid phase on all of the trays below. The molar ratio of the water in the extraction agent to the ethanol in the feed to the second column may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

Other suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with a portion of third residue in line 131, either prior to hydration or after, and co-fed to the second column 123.

Second column 123 may be a tray column having from 5 to 70 trays or packed column. Although the temperature and pressure of second column 123 may vary, when at atmospheric pressure the temperature of the second residue exiting in line 126 is from 60° C. to 90° C., e.g., from 70° C. to 90° C. The temperature of the second distillate exiting in line 127 is from 50° C. to 90° C., e.g., from 60° C. to 80° C. In general, column 123 operates at atmospheric pressure, but also may operate over the range from 0.1 kPa to 510 kPa. Exemplary components for the distillate and residue compositions for second column 123 are provided in Table 4 below.

TABLE 4

SECOND COLUMN 123 (FIG. 2)

|  | Conc. (wt. %) | Conc. (wt. %) | Conc. (wt. %) |
|---|---|---|---|
| Distillate |  |  |  |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |

TABLE 4-continued

SECOND COLUMN 123 (FIG. 2)

|  | Conc. (wt. %) | Conc. (wt. %) | Conc. (wt. %) |
|---|---|---|---|
| Ethanol | <30 | 0.001 to 15 | 0.01 to 5 |
| Acetal | <5 | 0.001 to 2 | 0.01 to 1 |
| Residue |  |  |  |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to second distillate preferably is at least 3:1, e.g., at least 6:1, or at least 15:1. All or a portion of the third residue is recycled to the second column. In one embodiment, all of the third residue may be recycled until system 100 reaches a steady state and then a portion of the third residue is recycled with the remaining portion being purged from system 100. The composition of the second residue will tend to have lower amounts of ethanol than when the third residue is not recycled. As the third residue is recycled, the composition of the second residue, as provided in Table 4, comprises less than 30 wt. % of ethanol. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from second column 123, which comprises ethanol and water, is fed via line 126 to third column 130, also referred to as the "product column." More preferably, the second residue in line 126 is introduced in the lower part of third column 130. Third column 130 recovers ethanol, which preferably is substantially pure with respect to organic impurities and other than the azeotropic water content, as the distillate in line 132. The distillate of third column 130 preferably is refluxed as shown in FIG. 2, for example, at a reflux ratio from 1:10 to 10:1.

Third column 130 is preferably a tray column as described above and operates at atmospheric pressure or optionally at pressures above or below atmospheric pressure. The temperature of the third distillate exiting in line 132 preferably is from 60° C. to 110° C., e.g., from 70° C. to 100° C. The temperature of the third residue in line 131 preferably is from 70° C. to 115° C., e.g., from 80° C. to 110° C. Exemplary components of the distillate and residue compositions for third column 130 are provided in Table 5 below.

TABLE 5

THIRD COLUMN 130 (FIG. 2)

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <12 | 0.0001 to 0.1 | 0.005 to 0.05 |
| Ethyl Acetate | <12 | 0.0001 to 0.05 | 0.005 to 0.025 |
| Acetaldehyde | <12 | 0.0001 to 0.1 | 0.005 to 0.05 |
| Diethyl Acetal | <12 | 0.0001 to 0.05 | 0.005 to 0.025 |
| Residue |  |  |  |
| Water | 75 to 100 | 80 to 99.8 | 90 to 99.7 |
| Ethanol | <0.8 | 0.001 to 0.5 | 0.005 to 0.05 |

TABLE 5-continued

| THIRD COLUMN 130 (FIG. 2) | | | |
|---|---|---|---|
| | Conc. (wt. %) | Conc. (wt. %) | Conc. (wt. %) |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition. In one embodiment, one or more side streams may remove impurities from any of the columns in system 100. Preferably at least one side stream is used to remove impurities from the third column 130.

Turning to hydration reaction zone 103, a portion of the third residue in line 131 may be contacted with an olefin feed stream 140, preferably comprising ethylene, in a hydration reactor 141. The third residue is a dilute alcohol stream due to the low ethanol concentration. The hydration reaction is carried out under the conditions described in herein. In one embodiment, the portion of the third residue in line 131 may be withdrawn from third column 130 in the vapor phase. When not in the vapor phase, an optional vaporizer 142 may be used. The resulting stream in line 143 from the hydration reactor is withdrawn and separated into an olefin stream 144 and an alcohol recovery stream 145. Any suitable separation may be used, such as a flasher, distillation column, or membrane. Typically olefin conversion may be low and thus the olefin stream 144 is returned to the hydration reactor 141.

Alcohol recovery stream 145 is enriched in ethanol as compared to the third residue in line 131. In one embodiment, alcohol recovery stream 145 may be separated to recover the ethanol and purge the water as necessary. In another embodiment, alcohol recovery stream 145 is fed to second column 123 as an extractive agent via line 124. In one embodiment, alcohol recovery stream 145 is withdrawn from hydration reactor 141 at a temperature higher than the operating temperature of second column 123. Preferably, the alcohol recovery stream 145 is integrated to heat one or more other streams or is reboiled prior to be returned to second column 123.

In one embodiment, a portion of third residue in line 131 may be purged via line 133. Once the process reaches steady state, a portion of water to be purged is substantially similar to the amount of water formed in the hydrogenation of acetic acid minus the water consumed during the hydration reaction.

The third residue in line 131, which comprises primarily water may bypass hydration reaction zone 103 and may be directed to second column 123 as an extraction agent as described above. In one embodiment, a first portion of the third residue in line 131 is recycled to second column 123 and a second portion is purged and removed from the system via line 133. In some embodiments, a portion of alcohol recovery stream 145 may be used to hydrolyze any other stream, such as one or more streams comprising ethyl acetate.

Although FIG. 2 shows alcohol recovery stream 145 being directly recycled to second column 123, alcohol recovery stream 145 may also be returned indirectly, for example, by storing a portion or all in a tank (not shown) or treating alcohol recovery stream 145 to further separate any minor components such as aldehydes, higher molecular weight alcohols, or esters in one or more additional columns (not shown).

In an optional embodiment, a portion of second residue in line 126 may be contacted with an olefin feed stream prior to third column 130. In those embodiments, hydration reaction zone 103 may be located between the second column 123 and third column 130. The resulting stream from the hydration of the olefin feed stream may be separated to recover the ethanol product stream in third column 130. If an olefin other than ethylene is used, the other alcohol may be withdrawn as a sidestream from third column 130.

The third distillate in line 132 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

In another embodiment, third distillate in line 132 may be reacted with an olefin feed stream as shown in FIG. 1C to reduce the water concentration of third distillate in line 132. Preferably third distillate in line 132 is reacted with the olefin feed stream prior to condensation. The resulting stream from the hydration reaction is refluxed as needed and a dehydrated ethanol product is recovered therefrom. The dehydrated ethanol product may contain less water than the third distillate in line 132.

Returning to second column 123, the second distillate preferably is refluxed as shown in FIG. 2, optionally at a reflux ratio of 1:10 to 10:1. The second distillate in line 127 may be purged or recycled to the reaction zone. In one embodiment, the second distillate in line 127 is further processed in fourth column 134, also referred to as the "acetaldehyde removal column." In fourth column 134 the second distillate is separated into a fourth distillate, which comprises acetaldehyde, in line 135 and a fourth residue, which comprises ethyl acetate, in line 136. The fourth distillate preferably is refluxed at a reflux ratio from 1:20 to 20:1, and a portion of the fourth distillate may be returned to reaction zone. Without being bound by theory, since acetaldehyde may be hydrogenated to form ethanol, the recycling of a stream that contains acetaldehyde to the reaction zone increases the yield of ethanol and decreases byproduct and waste generation. In another embodiment, the acetaldehyde may be collected and used, with or without further purification, to make useful products including but not limited to n-butanol, 1,3-butanediol, and/or crotonaldehyde and derivatives.

The fourth residue of fourth column 134 may be purged. The fourth residue primarily comprises ethyl acetate and ethanol, which may be suitable for use as a solvent mixture or in the production of esters. In one preferred embodiment, the acetaldehyde is removed from the second distillate in fourth column 134 such that no detectable amount of acetaldehyde is present in the residue of column 134.

Fourth column 134 is preferably a tray column as described above and preferably operates above atmospheric pressure. In one embodiment, the pressure is from 120 kPa to 5,000 kPa, e.g., from 200 kPa to 4,500 kPa. The temperature of the fourth distillate exiting in line 135 preferably is from 60° C. to 110° C., e.g., from 70° C. to 100° C. The temperature of the residue in line 136 preferably is from 70° C. to 115° C., e.g., from 80° C. to 110° C. Exemplary components of the distillate and residue compositions for fourth column 134 are provided in Table 6 below.

TABLE 6

FOURTH COLUMN 134 (FIG. 2)

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

The distillate and residue, due to the presence of water, of fourth column 134 may also be contacted with an olefin feed stream under hydration reaction conditions.

FIG. 3 illustrates another exemplary separation system. Hydration reaction zone 103 is placed after the water separation between the first column 150 and second column 154. Hydrogenation reaction zone 101 of FIG. 3 is similar to that of FIG. 2. Reaction zone 101 produces liquid stream 112, e.g., crude ethanol stream. In one preferred embodiment, reaction zone 101 of FIG. 3 preferably operates at above 80% acetic acid conversion, e.g., above 90% conversion or above 99% conversion. Thus, the acetic acid concentration in the liquid stream 112 may be low.

Liquid stream 112 is introduced in the middle or lower portion of first column 150, also referred to as acid-water column. For purposes of convenience, the columns in each exemplary separation process, may be referred as the first, second, third, etc., columns, but it is understood that first column 150 in FIG. 3 operates differently than the first column 120 of FIG. 2. In FIG. 3, first column 150, water and unreacted acetic acid, along with any other heavy components, if present, are removed from liquid stream 112 and are withdrawn, preferably continuously, as a first residue in line 151. Preferably, a substantial portion of the water in the crude ethanol stream that is fed to first column 150 may be removed in the first residue, for example, up to about 75% or to about 90% of the water from the crude ethanol stream. First column 150 also forms a first distillate, which is withdrawn in line 152.

When column 150 is operated under about 170 kPa, the temperature of the residue exiting in line 151 preferably is from 90° C. to 130° C., e.g., from 95° C. to 120° C. The temperature of the distillate exiting in line 152 preferably is from 60° C. to 90° C., e.g., from 65° C. to 85° C. In some embodiments, the pressure of first column 150 may range from 0.1 kPa to 510 kPa.

The first distillate in line 152 comprises water, in addition to ethanol and other organics. In terms of ranges, the concentration of water in first distillate in line 152 preferably is from 4 wt. % to 38 wt. %. A portion of first distillate in line 153 may be condensed and refluxed, for example, at a ratio from 10:1 to 1:10. It is understood that reflux ratios may vary with the number of stages, feed locations, column efficiency and/or feed composition. The condensed portion of the first distillate may also be fed to second column 154.

The remaining portion of the first distillate in 155 is fed to a water separation unit 156. Water separation unit 156 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In an exemplary embodiment, water separator 156 is a pressure swing adsorption (PSA) unit. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 156 may remove at least 95% of the water from the portion of first distillate in line 155, and more preferably from 99% to 99.99% of the water from the first distillate, in a water stream 157.

In one embodiment, a portion of water stream 157 may be contacted with an olefin feed stream 140, preferably comprising ethylene, in a hydration reactor 141. Water stream 157 may be a dilute alcohol stream due to the low concentrations of ethanol. The hydration reaction is carried out under the conditions described in herein. In one embodiment, water stream 157 may be withdrawn from water separator 156 in the vapor phase. When not in the vapor phase an optional vaporizer 142 may be used. The resulting stream in line 143 from the hydration reactor is withdrawn and separated into an olefin stream 144 and an alcohol recovery stream 145. Any suitable separation may be used, such as a flasher, distillation column, or membrane. Typically olefin conversion may be low and thus the olefin stream 144 is returned to the hydration reactor 141.

Alcohol recovery stream 145 is enriched in ethanol as compared to the water stream 157. In one embodiment, alcohol recovery stream 145 may be fed to first column 150 to remove ethanol in the first distillate in line 152. The water from alcohol recovery stream 145 may be removed in the residue of first column 150.

A portion of water stream 157 not fed to hydration reactor 140 may be purged via line 159.

In another embodiment, a portion of first residue in line 151 may be contacted with olefin feed stream 140 in hydration reaction zone 103.

The remaining portion of first distillate exits the water separator 156 as ethanol mixture stream 160. Ethanol mixture stream 160 may have a low concentration of water of less than 10 wt. %, e.g., less than 6 wt. % or less than 2 wt. %. Exemplary components of ethanol mixture stream 160 and first residue in line 151 are provided in Table 7 below.

TABLE 7

FIRST COLUMN 150 WITH PSA (FIG. 3)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

Preferably, ethanol mixture stream 160 is not returned or refluxed to first column 150. The condensed portion of the first distillate in line 153 may be combined with ethanol mixture stream 160 to control the water concentration fed to the second column 154. For example, in some embodiments the first distillate may be split into equal portions, while in other embodiments, all of the first distillate may be condensed or all of the first distillate may be processed in the water separation unit. In FIG. 3, the condensed portion in line 153 and ethanol mixture stream 160 are co-fed to second column 154. In other embodiments, the condensed portion in line 153 and ethanol mixture stream 160 may be separately fed to second column 154. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 154 in FIG. 3, also referred to as the "light ends column," removes ethyl acetate and acetaldehyde from the first distillate in line 152 and/or ethanol mixture stream 160. Ethyl acetate and acetaldehyde are removed as a second distillate in line 161 and ethanol is removed as the second residue in line 162. Second column 154 may be a tray column, having from 5 to 70 trays, or packed column.

Second column 154 operates at a pressure ranging from 0.1 kPa to 510 kPa. Although the temperature of second column 154 may vary, when at about 20 kPa to 70 kPa, the temperature of the second residue exiting in line 162 preferably is from 30° C. to 75° C., e.g., from 35° C. to 70° C. The temperature of the second distillate exiting in line 161 preferably is from 20° C. to 55° C., e.g., from 25° C. to 50° C.

Optionally, when first distillate in line 153 and/or ethanol mixture stream 160 comprises less than 1 wt. % water, additional water may be fed to the second column 154 as an extractive agent in the upper portion of the column. A sufficient amount of water is preferably added via the extractive agent such that the total concentration of water fed to second column 154 is from 1 to 10 wt. % water, e.g., from 2 to 6 wt. %, based on the total weight of all components fed to second column 154. If the extractive agent comprises water, the water may be obtained from an external source or from an internal return/recycle line from one or more of the other columns or water separators. Other extractive agents are described herein.

Exemplary components for the second distillate and second residue compositions for the second column 154 are provided in Table 8, below.

TABLE 8

SECOND COLUMN 154 (FIG. 3)

|  | Conc. (wt. %) | Conc. (wt. %) | Conc. (wt. %) |
| --- | --- | --- | --- |
| Second Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 97 | 60 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second residue in FIG. 3 comprises one or more impurities selected from the group consisting of ethyl acetate, acetic acid, acetaldehyde, and diethyl acetal. The second residue may comprise at least 100 wppm of these impurities. In some embodiments, the second residue may contain substantially no ethyl acetate or acetaldehyde.

The second distillate in line 161, which comprises ethyl acetate and/or acetaldehyde, preferably is refluxed as shown in FIG. 3, for example, at a reflux ratio from 1:30 to 30:1. In one aspect, not shown, the second distillate in line 161 or a portion thereof may be returned to reactor 108. The ethyl acetate and/or acetaldehyde in the second distillate may be further reacted in reactor 108.

In one embodiment, the second distillate in line 161 and/or a refined second distillate, or a portion of either or both streams, may be further separated to produce an acetaldehyde-containing stream and an ethyl acetate-containing stream. This may allow a portion of either the resulting acetaldehyde-containing stream or ethyl acetate-containing stream to be recycled to reactor 108 while purging the other stream. The purge stream may be valuable as a source of either ethyl acetate and/or acetaldehyde.

In another embodiment, second residue in line 162 may be reacted with an olefin feed stream as shown in FIG. 1C to reduce the water concentration of second residue in line 162. Preferably second residue in line 162 is reacted with the olefin feed stream in the vapor phase and second residue may be withdrawn as a vapor stream or vaporized as needed. The resulting stream from the hydration reaction is refluxed as needed and a dehydrated ethanol product is recovered therefrom. The dehydrated ethanol product may contain less water than the second residue in line 162.

The hydrogenation reaction zone 101 of FIG. 4 is similar to that of FIGS. 2 and 3 and produces liquid stream 112, e.g., crude ethanol stream, for further separation. In one preferred embodiment, the reaction zone 101 of FIG. 4 operates at above 80% acetic acid conversion, e.g., above 90% conversion or above 99% conversion. Thus, the acetic acid concentration in liquid stream 112 may be low.

Liquid stream 112 from separator 110 is withdrawn and directed as a feed composition to the side of first distillation column 170, also referred to as a "light ends column." Liquid stream 112 may be adjusted to have a temperature of up to 70° C. In the embodiment shown in FIG. 4, liquid stream 112 is introduced in the upper part of first column 170. An ethyl acetate recycle stream 191 may also be fed to first column 170 as shown in FIG. 4.

An optional extractive agent 171, which is the resulting stream from the hydration reaction zone 103 described below, may also be used and is preferably introduced above liquid stream 112. Extractive agent 171 may be adjusted to have a temperature of up to 70° C.

Extractive agent 171 preferably comprises water that has been retained within the system. As described herein, extractive agent 171 may be obtained from a portion of the second residue after hydration of the second residue. Extractive agent 171 may be a dilute acid stream comprising up to 20 wt. % acetic acid. Also because extractive agent 171 is from the hydration reaction, it may also comprise up to 20 wt. % ethanol. In one embodiment, the mass flow ratio of water in extractive agent 171 to the mass flow of the organic feed, which comprises liquid stream 112 and ethyl acetate recycle stream 191, may range from 0.05:1 to 2:1.

In one embodiment, first column 170 is a tray column having from 5 to 90 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 170 is operated under 50 kPa, the temperature of the residue exiting in line 172 preferably is from 20° C. to 100° C., e.g., from 30° C. to 90° C. The base of column 170 may be maintained at a relatively low temperature by withdrawing a residue stream comprising ethanol, ethyl acetate, water, and acetic acid, thereby providing an energy efficiency advantage. The temperature of the distillate exiting in line 173 from column 170 preferably at 50 kPa is from 10° C. to 80° C., e.g., from 20° C. to 70° C. The pressure of first column 170 may range from 0.1 kPa to 510 kPa.

In first column 170, a weight majority of the ethanol, water, acetic acid, are removed from the organic feed, including liquid stream 112 and ethyl acetate recycle stream 191, and are withdrawn, preferably continuously, as residue in line 172. This includes any water and ethanol added as an extractive agent 171. First column 170 also forms a distillate in line 173 that may be condensed and refluxed, for example, at a ratio from 30:1 to 1:30. Optionally, higher mass flow ratios of water, as an optional extractant, to organic feed may allow first column 170 to operate with a reduced reflux ratio. First distillate in line 173 preferably comprises a weight majority of the acetaldehyde and ethyl acetate from liquid stream 112, as well as from ethyl acetate recycle stream 191.

Exemplary components of the distillate and residue compositions for first column 170 are provided in Table 9 below.

TABLE 9

LIGHT ENDS COLUMN (FIG. 4)

| | Conc. (wt. %) | Conc. (wt. %) | Conc. (wt. %) |
|---|---|---|---|
| Distillate | | | |
| Ethyl Acetate | 10 to 85 | 15 to 80 | 20 to 75 |
| Acetaldehyde | 0.1 to 70 | 0.2 to 65 | 0.5 to 65 |
| Acetal | <3 | 0.01 to 2 | 0.05 to 1.5 |
| Acetone | <0.05 | 0.001 to 0.03 | 0.01 to 0.025 |
| Ethanol | <25 | 0.001 to 20 | 0.01 to 15 |
| Water | 0.1 to 20 | 1 to 15 | 2 to 10 |
| Acetic Acid | <2 | <0.1 | <0.05 |
| Residue | | | |
| Acetic Acid | 0.01 to 50 | 0.5 to 40 | 1 to 30 |
| Water | 20 to 85 | 25 to 80 | 30 to 75 |
| Ethanol | 10 to 75 | 15 to 70 | 20 to 65 |
| Ethyl Acetate | 0.005 to 30 | 0.03 to 25 | 0.08 to 1 |

The weight ratio of water in the residue in line 172 to water in the distillate in line 173 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 108. In one embodiment, when the conversion in the hydrogenation reactor is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The first distillate in line 173 preferably is substantially free of acetic acid, e.g., comprising less than 1000 wppm acetic acid. The distillate may be purged from the system or recycled in whole or part to reactor 108.

To recover ethanol, first residue in line 172 may be further separated depending on the concentration of acetic acid and/or ethyl acetate. In most embodiments of the present invention, residue in line 172 is further separated in a second column 180, also referred to as an "acid column." Second column 180 yields a second residue in line 181 comprising acetic acid and water, and a second distillate in line 182 comprising ethanol and ethyl acetate. In one embodiment, a weight majority of the water and/or acetic acid fed to second column 180 is removed in the second residue in line 181, e.g., at least 60% of the water and/or acetic acid is removed in the second residue in line 181 or more preferably at least 80% of the water and/or acetic acid. Second column 180 also forms a second distillate in line 182 which may be condensed and refluxed, for example, at a ratio from 12:1 to 1:12.

Optionally, first residue in line 172 may be preheated prior to being introduced into second column 180. The first residue in line 172 may be heat integrated with either the residue or vapor overhead of the second column 180.

Second column 180 operates in a manner to concentrate the ethanol from first residue so that a majority of the ethanol is carried overhead. Thus, the residue of second column 180 may have a low ethanol concentration as shown in Table 10 below. Lower ethanol concentrations may be achieved without significant increases in reboiler duty or column size. Thus, in some embodiments it is efficient to reduce the ethanol concentration in the residue to less than 50 wppm.

In FIG. 4, the first residue in line 172 is introduced to second column 180 preferably in the top part of column 180. Acid column 180 may be a tray column having from 10 to 110 theoretical trays or packed column. Although the temperature and pressure of second column 180 may vary, when at atmospheric pressure the temperature of the second residue in line 181 preferably is from 95° C. to 160° C., e.g., from 100° C. to 150° C. or from 110° C. to 145° C. The temperature of the second distillate exiting in line 182 from second column 180 preferably is from 50° C. to 120° C., e.g., from 75° C. to 118° C. or from 80° C. to 115° C.

The pressure of second column 180 may range from 0.1 kPa to 510 kPa, e.g., from 1 kPa to 475 kPa or from 1 kPa to 375 kPa. In one embodiment, second column 180 operates above atmospheric pressure, e.g., above 170 kPa or above 375 kPa. Second column 180 may be constructed of a material such as 316L SS, Allot 2205 or Hastelloy C, depending on the operating pressure.

Exemplary components for the distillate and residue compositions for second column 180 are provided in Table 10 below. For example, in optional embodiments, when ethyl acetate is in the feed to reactor 108, second residue in line 181 exemplified in Table 10 may also comprise high boiling point components.

TABLE 10

ACID COLUMN (FIG. 4)

| | Conc. (wt. %) | Conc. (wt. %) | Conc. (wt. %) |
|---|---|---|---|
| Second Distillate | | | |
| Ethanol | 80 to 96 | 85 to 92 | 87 to 90 |
| Ethyl Acetate | <30 | 0.001 to 15 | 0.005 to 4 |
| Acetaldehyde | <20 | 0.001 to 15 | 0.005 to 4 |
| Water | <20 | 0.001 to 10 | 0.01 to 8 |
| Acetal | <2 | 0.001 to 1 | 0.005 to 0.5 |

TABLE 10-continued

ACID COLUMN (FIG. 4)

| | Conc. (wt. %) | Conc. (wt. %) | Conc. (wt. %) |
|---|---|---|---|
| Second Residue | | | |
| Acetic Acid | 0.1 to 55 | 0.2 to 40 | 0.5 to 35 |
| Water | 45 to 99.9 | 55 to 99.8 | 65 to 99.5 |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in second distillate in line 182 to ethanol in the second residue in line 181 preferably is at least 35:1. Preferably, second distillate in line 182 is substantially free of acetic acid and may contain, if any, trace amounts of acetic acid.

In one embodiment, ethyl acetate fed to second column 180 may concentrate in the second distillate in line 182. Thus, preferably no ethyl acetate is withdrawn in the second residue in line 181.

As discussed above, according to the present invention, unreacted acetic acid may be concentrated in the second residue in line 181. The second residue in line 181 may comprise from 85% to 99.99% of the unreacted acetic acid from the crude ethanol stream 109. In one embodiment, substantially all of the unreacted acetic acid is recovered in the second residue in line 181. By removing substantially all of the unreacted acetic acid from crude ethanol stream 109, the process, in some aspects, advantageously does not require further separation of acetic acid from the ethanol. In some embodiments, the dilute acid stream comprises from 0.1 to 55 wt. % acetic acid and from 45 to 99 wt. % water.

In one embodiment, a portion of the second residue in line 181 may be contacted with an olefin feed stream 140, preferably comprising ethylene, in a hydration reactor 141. The third residue is a dilute alcohol stream due to the low ethanol concentration. The hydration reaction is carried out under the conditions described herein. In one embodiment, a portion of the second residue in line 181 may be withdrawn from second column 180 in the vapor phase. When not in the vapor phase, an optional vaporizer 142 may be used. The resulting stream in line 143 from the hydration reactor is withdrawn and separated into an olefin stream 144 and an alcohol recovery stream 145. Any suitable separation may be used, such as a flasher, distillation column, or membrane. Typically olefin conversion may be low and thus the olefin stream 144 is returned to the hydration reactor 141.

Alcohol recovery stream 145 is enriched in ethanol as compared to the second residue in line 181. In one embodiment, alcohol recovery stream 145 may be separated to recover the ethanol and purge the water as necessary. In another embodiment, alcohol recovery stream 145 is fed to first column 170 as an extractive agent 171. In one embodiment, alcohol recovery stream 145 is withdrawn from hydration reactor 141 at a temperature higher than the operating temperature of first column 170. Preferably, the alcohol recovery stream 145 is integrated to heat one or more other streams or is reboiled prior to be returned to first column 170.

The second residue in line 181, which comprises primarily water, preferably is returned via line 171 to first column 170 as an extraction agent as described above. In one embodiment, a portion of second residue is purged and removed from the system via line 183. In one embodiment, once the process reaches steady state, the second portion of water to be purged is substantially similar to the amount water formed in the hydrogenation of acetic acid minus the water consumed during the hydration reaction. In some embodiments, a portion of alcohol recovery stream 145 may be used to hydrolyze any other stream, such as one or more streams comprising ethyl acetate or diethyl acetal.

In an optional embodiment, a portion of first residue in line 172 may be contacted with an olefin feed stream prior to second column 180. The resulting stream from the hydration of the olefin feed stream may be separated to recover the ethanol product stream in second column 170. If an olefin other than ethylene is used, the other alcohol may be withdrawn as a sidestream from second column 170.

In one embodiment, as shown in FIG. 4, due to the presence of ethyl acetate in second distillate in line 182, an additional third column 190 may be used. A third column 190, referred to as a "product" column, is used for removing ethyl acetate from second distillate in line 182 and producing an ethanol product in the third residue in line 192. Product column 190 may be a tray column having from 5 to 90 theoretical trays or packed column.

The feed location of second distillate in line 182 may vary and it is preferred to feed second distillate in line 182 to the upper portion of third column 190. Second distillate in line 182 may be fed to third column 190 at a temperature of up to 70° C.

Ethyl acetate may be concentrated in the third distillate in line 191. Due to the relatively lower amounts of ethyl acetate fed to third column 190, third distillate in line 191 also comprises substantial amounts of ethanol. To recover the ethanol, third distillate in line 191 may be fed to first column as an ethyl acetate recycle stream 191. Depending on the ethyl acetate concentration of ethyl acetate recycle stream 191 this stream may be introduced above or near the feed point of the liquid stream 112. Depending on the targeted ethyl acetate concentration in the distillate of first column 170 the feed point of ethyl acetate recycle stream 191 will vary. Liquid stream 112 and ethyl acetate recycle stream 191 collectively comprise the organic feed to first column 170. In one embodiment, organic feed comprises from 1 to 25% of ethyl acetate recycle stream 191. This amount may vary depending on the production of reactor 108 and amount of ethyl acetate to be recycled.

Because ethyl acetate recycle stream 191 increases the demands on the first and second columns, it is preferred that the ethanol concentration in third distillate in line 191 be from 70 to 90 wt. %, e.g., from 72 to 88 wt. %, or from 75 to 85 wt. %. In other embodiments, a portion of third distillate in line 191 may be purged from the system in line 193 as additional products, such as an ethyl acetate solvent. In addition, ethanol may be recovered from a portion of the third distillate in line 191 using an extractant, such as benzene, propylene glycol, and cyclohexane, so that the raffinate comprises less ethanol to recycle.

In an optional embodiment, the third residue may be further processed to recover ethanol with a desired amount of water, for example, using a further distillation column, adsorption unit, membrane or combination thereof, may be used to further remove water from third residue in line 192 as necessary.

Third column 190 is preferably a tray column as described above and preferably operates at atmospheric pressure. The temperature of the third residue in line 192 exiting from third column 190 preferably is from 65° C. to 110° C., e.g., from 70° C. to 100° C. The temperature of the third distillate in line 191 exiting from third column 190 preferably is from 30° C. to 70° C., e.g., from 40° C. to 65° C. The pressure of third column 190 may range from 0.1 kPa to 510 kPa. Exemplary components for ethanol mixture stream and residue compositions for third column 190 are provided in Table 11 below.

TABLE 11

PRODUCT COLUMN (FIG. 4)

|  | Conc. (wt. %) | Conc. (wt. %) | Conc. (wt. %) |
|---|---|---|---|
| Third Distillate |  |  |  |
| Ethanol | 70 to 99 | 72 to 95 | 75 to 90 |
| Ethyl Acetate | 1 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue |  |  |  |
| Ethanol | 80 to 99.5 | 85 to 97 | 90 to 95 |
| Water | <3 | 0.001 to 2 | 0.01 to 1 |
| Ethyl Acetate | <1.5 | 0.0001 to 1 | 0.001 to 0.5 |
| Acetic Acid | <0.5 | <0.01 | 0.0001 to 0.01 |

In another embodiment, third residue in line 192 may be reacted with an olefin feed stream as shown in FIG. 1C to reduce the water concentration of third residue in line 192. Preferably third residue in line 192 is reacted with the olefin feed stream prior to condensation. The resulting stream from the hydration reaction is refluxed as needed and a dehydrated ethanol product is recovered therefrom. The dehydrated ethanol product may contain less water than the third residue in line 192.

In another embodiment, water may be removed prior to recovering the ethanol product as described above in FIG. 3 with the water separator 156. Second column 180 forms an overhead, which may comprise 85 to 92 wt. % ethanol, e.g., 87 to 90 wt. % ethanol, with the remaining balance being water and ethyl acetate. In one embodiment, the overhead may comprise less than 15 wt. % water, e.g., less than 10 wt. % water or less than 8 wt. % water. Overhead vapor from second column 180 may be fed to a water separator (not shown), as described above. Water separator may be an adsorption unit, membrane, molecular sieves, light ends column distillation, or a combination thereof. In one embodiment, at least 50% of overhead vapor is fed to water separator. In another embodiment, the water separator may also be combined with a second hydration reactor as described above in FIG. 3.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The ethanol product produced by the process of the present invention may be an industrial grade ethanol comprising from 85 to 96 wt. % ethanol, based on the total weight of the ethanol product. In some embodiments, when further water separation is used, the ethanol product may be withdrawn as a stream from the water separation unit as discussed above. In such embodiments, the ethanol concentration of the ethanol product may be higher, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %. Exemplary finished ethanol compositional ranges are provided below in Table 12.

TABLE 12

FINISHED ETHANOL COMPOSITIONS

| Component | Conc. (wt. %) | Conc. (wt. %) | Conc. (wt. %) |
|---|---|---|---|
| Ethanol | 75 to 99.5 | 80 to 97 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

In one embodiment, the amount of isopropanol in the finished ethanol composition is from 80 to 1,000 wppm, e.g., from 95 to 1,000 wppm, from 100 to 700 wppm. The finished ethanol composition may be substantially free of acetaldehyde.

The finished ethanol composition produced by the embodiments of the present invention may be used in a variety of applications including applications as fuels, solvents, chemical feedstocks, pharmaceutical products, cleansers, sanitizers, hydrogen transport or consumption. The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

What is claimed is:

1. A process for producing an alcohol, comprising:
    hydrogenating an acetic acid feed stream in the presence of a first catalyst in a first reaction zone to form a crude alcohol product;
    separating at least a portion of the crude alcohol product in one or more columns to produce an alcohol product stream and a dilute alcohol stream comprising water; and contacting an olefin feed stream with at least a portion of the dilute alcohol stream in the presence of a second catalyst in a second reaction zone to form an alcohol corresponding to the olefin.

2. The process of claim 1, further comprising introducing the alcohol corresponding to the olefin into the one or more columns.

3. The process of claim 1, wherein the dilute alcohol stream comprises more water, based on relative weight percent, than the alcohol product stream.

4. The process of claim 1, wherein the olefin feed stream comprises one or more olefins selected from the group consisting of ethylene, propylene, but-1-ene, pent-1-ene, and hex-1-ene.

5. The process of claim 1, wherein the hydrogenation step and contacting step produce the same alcohol.

6. The process of claim 1, wherein at least 5% of the water from the dilute alcohol stream is converted to the alcohol corresponding to the olefin.

7. The process of claim 1, wherein the molar ratio of water to olefin in the second reaction zone is from 0.5:1 to 20:1.

8. The process of claim 1, wherein the second reaction zone is conducted in the vapor phase.

9. The process of claim 1, wherein the second catalyst is selected from the group consisting of phosphoric acid, sulfuric acid, tungstic acid, heteropoly acid salt and anionic ion exchange resin.

10. The process of claim 1, wherein the temperature of the second reaction zone is from 150° C. to 600° C.

11. The process of claim 1, wherein the pressure of the second reaction zone is from 1 MPa to 25 MPa.

12. The process of claim 1, further comprising dehydrating a portion of the alcohol product to produce the olefin feed stream.

13. The process of claim 1, wherein the first catalyst comprises:
a first metal selected from the group consisting of cobalt, nickel, rhodium, palladium, osmium, iridium, platinum, titanium, zinc, chromium, rhenium, molybdenum, and tungsten;
a second metal selected from the group consisting of molybdenum, tin, chromium, cobalt, vanadium, tungsten, palladium, platinum, lanthanum, cerium, manganese, rhenium, gold, and nickel, provided that the second metal is different than the first metal; and
a support.

14. The process of claim 13, wherein the first catalyst further comprises at least one support modifier selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

15. The process of claim 14, wherein the support modifier is calcium metasilicate.

16. The process of claim 14, wherein the support modifier is selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $Nb_2O_5$, $MnO_2$, $CuO$, $Co_2O_3$, and $Bi_2O_3$.

17. A process for producing ethanol, comprising:
hydrogenating an acetic acid feed stream in the presence of a first catalyst in a first reaction zone to form a first crude product comprising ethanol and water;
contacting an olefin feed stream with at least a portion of the first crude product in the presence of a second catalyst in a second reaction zone to form a second crude product, wherein the second crude product comprises less water than the first crude product; and
recovering ethanol from the second crude product.

18. The process of claim 17, wherein the conversion of acetic acid in the first reaction zone is greater than 90%.

19. The process of claim 17, wherein the water concentration of the first crude product is reduced by at least 5 wt. %.

20. A process for producing ethanol, comprising:
hydrogenating an acetic acid feed stream in the presence of a first catalyst in a first reaction zone to form a crude ethanol stream;
separating at least a portion of the crude ethanol stream in one or more columns to yield an ethanol product and a water stream; and
contacting an olefin feed stream with at least a portion of the ethanol product in the presence of a second catalyst in a second reaction zone to form a dehydrated ethanol product, wherein the dehydrated ethanol product comprises less water than the ethanol product.

* * * * *